United States Patent [19]

Okpanyi

[11] Patent Number: 5,618,537
[45] Date of Patent: Apr. 8, 1997

[54] PLANT-BASED MEDICAMENTS FOR INCREASING THE TONE AND MODULATING THE TONE OF THE SMOOTH MUSCULAR ORGAN

[75] Inventor: Samuel N. Okpanyi, Wiesbaden, Germany

[73] Assignee: Steigerwald Arzneimittelwerk GmbH, Darmstadt, Germany

[21] Appl. No.: 380,322

[22] Filed: Jan. 30, 1995

Related U.S. Application Data

[63] Continuation of Ser. No. 915,706, Jul. 29, 1992, abandoned.

[30] Foreign Application Priority Data

Jul. 29, 1991 [DE] Germany ............................ 41 25 024.9
Apr. 3, 1992 [WO] WIPO ...................... PCT/EP92/00751

[51] Int. Cl.⁶ ...................................................... A61K 35/78
[52] U.S. Cl. ............................................................ 424/195.1
[58] Field of Search ............................................ 424/195.1

[56] References Cited

U.S. PATENT DOCUMENTS 4,742,046  5/1988  Bliah ............................................ 514/8

OTHER PUBLICATIONS

Codington, J. F. et al., *Carbohydrate Research*, Mar. 1975 40(1), pp. 171–182.

Dahr, W. et al., *Vox San*, 1971, 21(4) pp. 338–351.

Grieve, M. A. *Modern Herbal*, vol. 1, p. 156, 1971, Dover Publications, Inc., NY.

*Primary Examiner*—John W. Rollins
*Attorney, Agent, or Firm*—Nikaido, Marmelstein, Murray & Oram LLP

[57] ABSTRACT

Plant-based medicament having tonicising action on smooth muscular organs which are atonic or have decreased tone. The medicament contains *Iberis amara*, preferably *Iberis amara* totalis (flowers, seeds, leaves, stalk and roots), in particular as a plant extract or its constituents, optionally together with one or more other constituents selected from the group consisting of *Menthae piperitae*, Matricariae, *Carvi fructus*, *Melissae folium* and *Liquiritiae radix*, as the sole carrier(s) of the activity. Methods of treating patients comprising administering the medicaments.

17 Claims, 6 Drawing Sheets

PLANT-BASED MEDICAMENTS FOR INCREASING THE TONE AND MODULATING THE TONE OF THE SMOOTH MUSCULAR ORGAN

This application is a continuation of application Ser. No. 07/915,706 filed Jul. 29, 1992, now abandoned.

FIELD OF THE INVENTION

The invention relates to a medicament having tonicising action on smooth muscular organs which are atonic or have decreased tone. It furthermore relates to such a medicament having tone-modulating action on organs of this type which have decreased tone or increased tone. Finally, it is aimed at the use of a medicament of this type as a base therapeutic.

BACKGROUND OF THE INVENTION

In gastroenterological diagnoses such as dyspepsia, functional gastrointestinal complaints, gastropathy and irritable colon, with complex and diverse symptoms, tone-related incorrect regulation of the gastrointestinal motor system or motility is important. Both cramps (spasms) and also hypotonic constipation (atonia) with decreased gastrointestinal emptying occur, accompanied by such disorders as pressure and pain in the upper abdomen, gastrocardiac pain, eructation, heartburn, sensation of fullness, oesophagitis and gastritis and even ulcers in the gastrointestinal tract.

In therapy, the chemical medicaments known are mainly those which have a spasmolytic anticholinergic effect or the chemical prokinetics and dopamine antagonists, which have side effects. A plant-based medicament is also known. The plant constituents it contains are compulsorily a mixture of *Iberis amara* totalis, alcoholic fresh plant extract, together with alcoholic drug extracts of *Angelicae radix, Cardui mariae* fructus, *Carvi fructus, Chelidonii herba, Liquiritiae radix, Matricariae flos, Melissae folium* and *Menthae piperitae* folium. There are therefore a relatively large number of active substances which the patient is forced to take.

SUMMARY OF THE INVENTION

The object of the invention is to provide a plant-based medicament having a limited number of active substances/constituents, in particular extracts, which has a fundamentally tone-increasing effect in the relaxed smooth musculature, in particular of the intestine.

This object is achieved according to the invention in that the medicament contains *Iberis amara*, preferably *Iberis amara* totalis (flowers, seeds, leaves, stalk and roots), in particular as a plant extract, as the sole carrier of the activity. It has surprisingly been shown that the active substances of this plant suffice, without any other assistance and active substances, both in the prophylactic and therapeutic respect for increasing the tone and motility in hypotonic smooth muscular organs, such as the gastrointestinal tract, gall bladder, urinary bladder, veins and uterus. The additional plant active substances previously held as necessary for achieving this action are thus unnecessary, and there is thus a substantially lower load on the patient than when the known medicaments are taken.

In continuation of the invention, it has also surprisingly been found that a plant-based medicament having tone-modulating action on smooth muscular organs which have decreased tone or increased tone is provided when, besides *Iberis amara*, preferably *Iberis amara* totalis (flowers, seeds, leaves, stalk and roots), in particular as a plant extract, it contains one or more other constituents of the group consisting of *Menthae piperitae* folium, *Matricariae flos, Carvi fructus, Melissae folium* and *Liquiritiae radix,* preferably as a plant extract, as the sole carrier of the activity. This medicament according to the invention is distinguished from the above-mentioned known plant-based medicaments in that in contrast it contains a reduced number of plant substances. Compared with the known medicaments, *Chelidonii herba, Cardui maria* fructus and *Angelicae radix* are not present. A whole series of, under certain circumstances, loading substances can be dispensed with in the treatment of patients. In spite of this, the medicament according to the invention is completely effective in the prophylactic and therapeutic respect for modulating or regulating the tone and motility in disorders of smooth muscular organs, such as the gastrointestinal tract, gall bladder, urinary bladder, veins and uterus, which disorders are of causal, or as a consequence of tone and motility disorders, various genesis. Besides *Iberis amara* totalis, the plants or their active substances used in the medicament according to the invention have, above all, a spasmolytic action and produce, in cooperation with *Iberis amara*, completely the desired effect of tone-modulating action on smooth muscular organs which have decreased tone or increased tone. The medicament according to the invention can be used both as a primary (causal) or secondary therapeutic, in particular in complaints of the gastrointestinal tract having the tone and motility disorders mentioned, both in hypotonic and hypertonic and in hypokinetic and hyperkinetic states.

According to preferred aspects of the invention, it is furthermore intended that the medicament is prepared in the form of plant extracts and consists essentially of 15–40% by volume of *Iberis amara,*

10–30% by volume of *Menthae piperitae,*

20–40% by volume of Matricariae,

10–30% by volume of *Carvi fructus,*

10–30% by volume of *Melissae folium* and

10–30% by volume of *Liquiritiae radix.*

A particularly preferred exemplary embodiment of the invention is distinguished in that the plant extracts are intended to be as follows:

15% by volume of *Iberis amara* totalis,

10% by volume of *Menthae piperitae* folium,

30% by volume of *Matricariae flos,*

20% by volume of *Carvi fructus,*

15% by volume of *Melissae folium* and

10% by volume of *Liquiritiae radix.*

The present invention also relates to a medicament consisting essentially of *Iberis amara.*

It is also within the scope of the invention if the plant extract, preferably *Iberis amara*, is a fresh plant extract. As a result of this, a number of active substances are added to the medicament which, in the preparation of a drug extract, could in certain circumstances be no longer completely present and thus no longer active. Even with the other plants present in the manner according to the invention in a reduced number compared with the prior art, fresh plant extracts can be prepared, although as a rule drug extracts are prepared from these plants.

According to the invention, in the fresh plant extract the ratio of macerated or percolated plants to the extracts is about 3 to 7, preferably 6 grams of *Iberis amara:*10 grams. In the drug extract, according to the invention, a ratio of drugs to extract of about 1.5 to 10 grams, preferably 3.5 grams:10 grams is envisaged. According to the invention, the extracting agent preferably used for the extracts is ethanol in a final concentration of 30 to 40% by volume, the remainder being $H_2O$.

Finally, it is within the scope of the invention to use the medicament according to the invention as a base therapeutic.

To summarise, it can be stressed that it has surprisingly been found that medicament according to the invention comprising *Iberis amara* as the sole carrier of activity and medicament according to the invention comprising *Iberis amara* and one or more constituents selected from the group consisting of *Menthae piperitae,* Matricariae, *Carvi fructus, Melissae folium* and *Liquiritiae radix* as the sole carriers of activity are just as active as and, in a particular respect, even more active than the medicament available on the market until now (STW 5), which—compared with medicament according to the invention comprising *Iberis amara* and one or more constituents selected from the group consisting of *Menthae piperitae,* Matricariae, *Carvi fructus, Melissae folium* and *Liquiritiae radix* as the sole carriers of activity— additionally contains *Chelidonii herba, Cardui mariae* fructus and *Angelicae radix*.

The functional gastrointestinal complaints are multifactorial occurrences in which the medicament according to the invention intervenes multilocally and accordingly, as further shown below, has been tested.

BRIEF DESCRIPTION OF THE DRAWING FIGURES

Other details, feature and advantages of the invention will emerge from the following description, the patent claims and the drawings, in which:

DETAILED DESCRIPTION OF THE INVENTION

Increase in Tone

The effect of *Iberis amara* fresh plant extract comprising *Iberis amara* as the sole carrier of activity, called STW 6 in the text which follows, on the tone of the intestine was tested using the classical pharmacological guinea-pig ileum model according to Magnus, R.: Versuche am überlebenden D ünndarm von Säugetieren, Ist communication, Pflügers Archiv Ges. Physiol. 102, 123–151 (1904), both on a resting and on an acetylcholine-stimulated piece of ileum in a 37° C. thermostated organ bath containing Krebs-Henseleit base solution with 95% $O_2$/5% $CO_2$ aeration. STW 6 is a plant extract obtained by extracting *Iberis amara* totalis alone (equals 100%). The extracting agent is ethanol in a final concentration of 35% by volume, the remainder being water.

Figure 1:
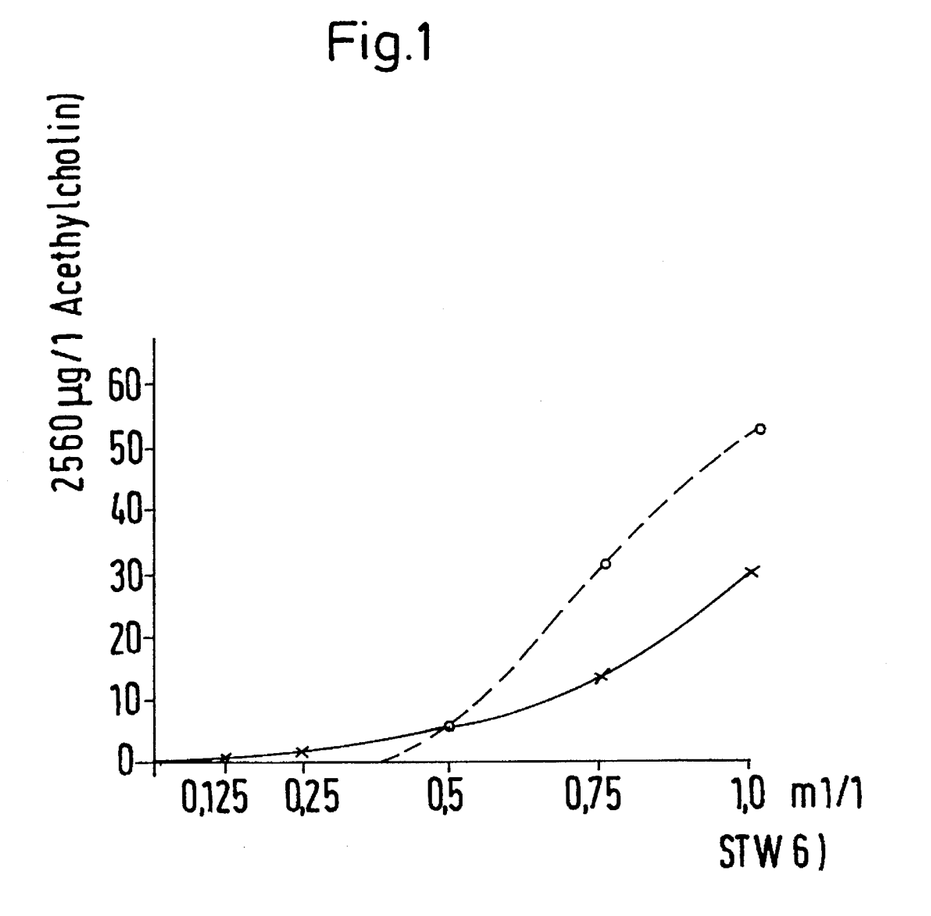
FIG. 1 shows the effect of medicament according to the invention comprising *Iberis amara* as the sole carrier of activity on the tone of resting isolated guinea-pig ileum.

STW 6 led in the resting/relaxed (atonic) guinea-pig ileum to a dose-dependent increase in basal tone (FIG. 1), and additionally to a fully reversible spontaneous contraction.

In an intestine stimulated with only a low acetylcholine concentration (2.5≦160 µg/l) (hypotonic state), STW 6 likewise causes a dose-dependent increase in tone. At higher acetylcholine doses (>160–640 µg/l), at which adequate tone and contraction prevail, STW 6 no longer has a tone-increasing action.

Motility of the Gastrointestinal Tract (Fresh Plant Extracts)

Investigations of the effect of *Iberis amara* fresh plant extract on the motility of the gastrointestinal tract in minipigs from Alaska-Hoke (body weight around 20–25 kg) were furthermore carried out. Under Nembutal anaesthesia, the animals were subjected to endoscopy and the test substances were applied to the gastric mucosa under endoscopic viewing.

The motility was determined by means of a probe and timer. In addition, the following parameters were determined: Acidity, according to Lanza, F. C.; Aspinall, R. L.; Swabb, E. A. et al.: A double-blind, placebo-controlled, endoscopic comparison of the cytoprotective effects of misoprostol and cimetidine in tolmetin-induced gastric mucosal injury. Clinical development of misoprostol: Peptic ulcer disease and NSAID induced gastropathy, Chicago, May 1987 and Davenport (1964), Tissue histamine, according to Lorenz, W.; Reimann, H.-J. et al.: A sensitive and specific method for the determination of histamine in human whole blood and plasma. Hoppe-Seyler's Z. Physiol. Chem. 353, 911–920 (1972), Mast cells, according to Mohri, K.; Reimann, H.-J. et al.: Histamine content and mast cells in human gastric and duodenal mucosa. Agents and Actions 8 (4), 372 (1978) and Prostaglandin ($PGE_2$), according to Moncada, S.; Herman, A. G. et al.: Differential formation of prostacyclin (PGX or $PGI_2$) by lysis of the arterial wall. An explanation for the anti-thrombotic properties of vascular endothelium. Thrombosis Research 11, 323–344 (1977).

The result of this investigation (Table 1) shows that *Iberis amara* increases the motility both of the stomach and of the intestine in a statistically significant manner. In addition, a cytoprotective action can be detected due to the statistically significant inhibition of acetylsalicylic acid-provoked tissue histamine release and mast cell proliferation.

The tone- and motility-regulating action of the medicament according of the invention comprising *Iberis amara* and one or more constituents selected from the group consisting of *Menthae piperitae,* Matricariae, *Carvi fructus, Melissae folium* and *Liquiritiae radix* as the sole carriers of activity, also called STW 5-II, containing a decreased number of constituents suitable as carriers of the activity compared with the known plant-based product (STW 5) was investigated. STW 5-II is a mixture of plant extracts comprising about 15% by volume of *Iberis amara* totalis, 10% by volume of *Menthae piperitae* folium, 30% by volume of *Matricariae flos,* 20% by volume of *Carvi fructus,* 15% by volume of *Melissae folium* and 10% by volume of *Liquiritiae radix,* in which the individual extracts have been obtained likewise as described above in connection with STW 6.

Increase in Basal Tone

The basal tone-increasing action of STW 5-II compared with STW 5 was verified using the classical pharmacological model of the guinea-pig ileum according to Magnus. In Tables 2 and 3 and FIGS. 2 and 3 respectively which represent them graphically, the results are presented compared with the contraction induced by acetylcholine, 40 μg/l.

Figure 2:
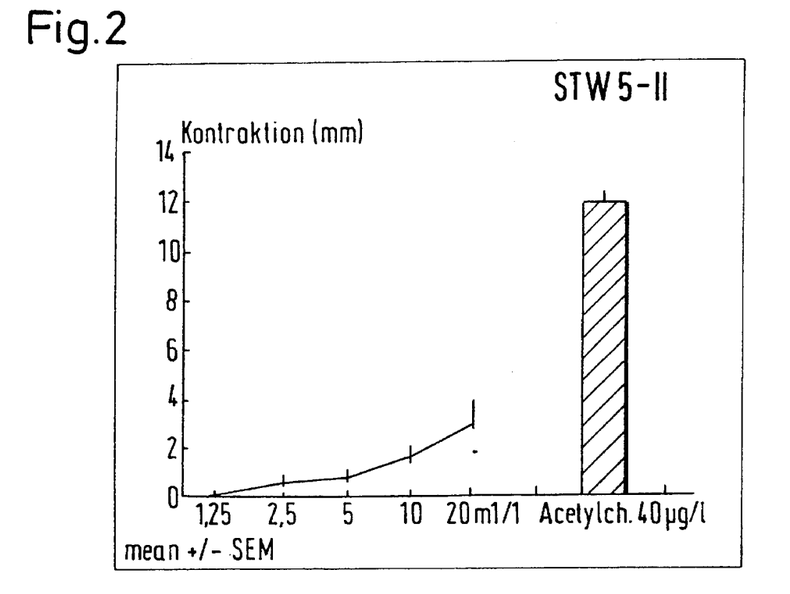
FIG. 2 shows the graphical representation of Table 2.
Figure 3:
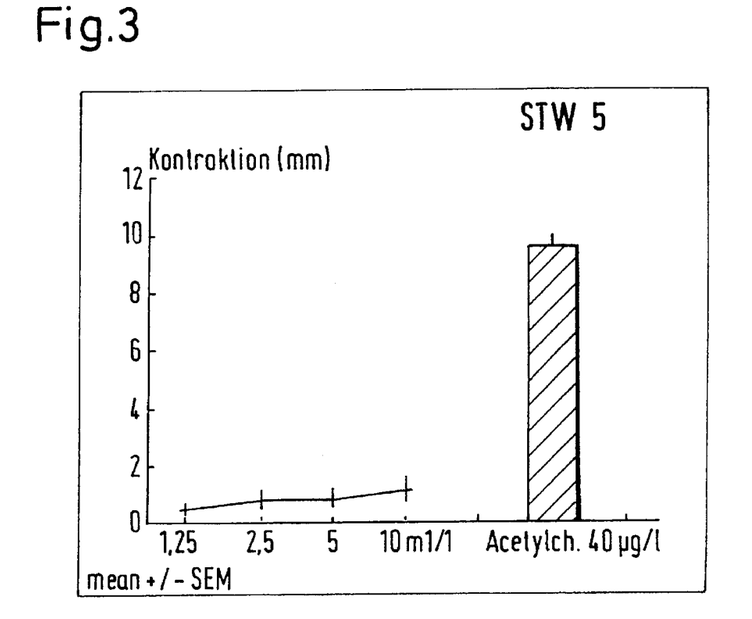
FIG. 3 shows the graphical representation of Table 3.
Figure 4:
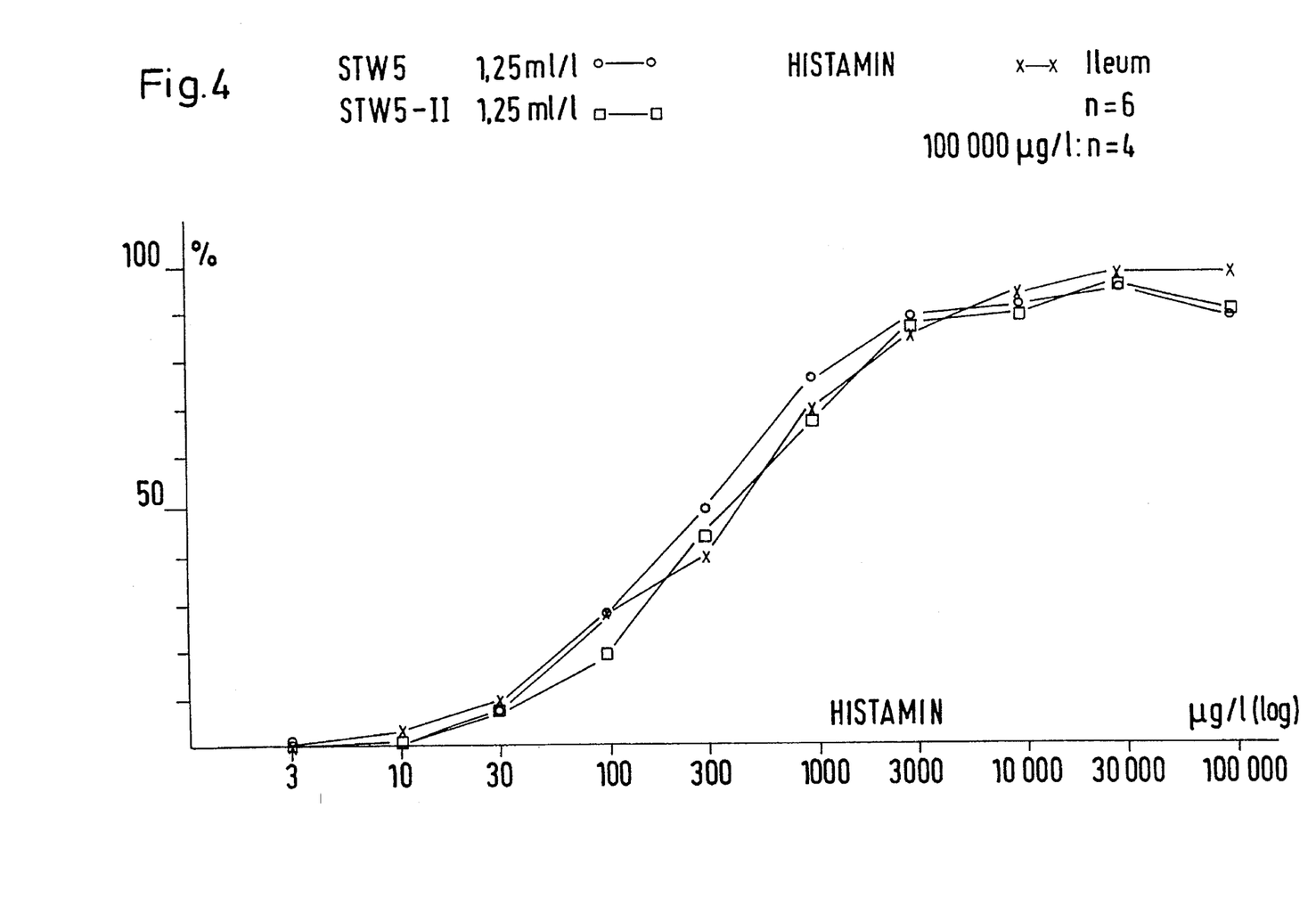
FIGS. 4–7 show the effect of the medicament according to the invention comprising *Iberis amara* and one or more constituents selected from the group consisting of *Menthae piperitae,* Matricariae, *Carvi fructus, Melissae folium* and *Liquiritiae radix* as the sole carriers of activity and a comparison of the effect of the medicament according to the invention comprising *Iberis amara* and one or more constituents selected from the group consisting of *Menthae piperitae,* Matricariae, *Carvi fructus, Melissae folium* and *Liquiritiae radix* as the sole carriers of activity compared with the known plant-based medicament (STW 5) on histamine-induced contraction (spasms) of the guinea-pig ileum at the different concentrations indicated.
Figure 5:
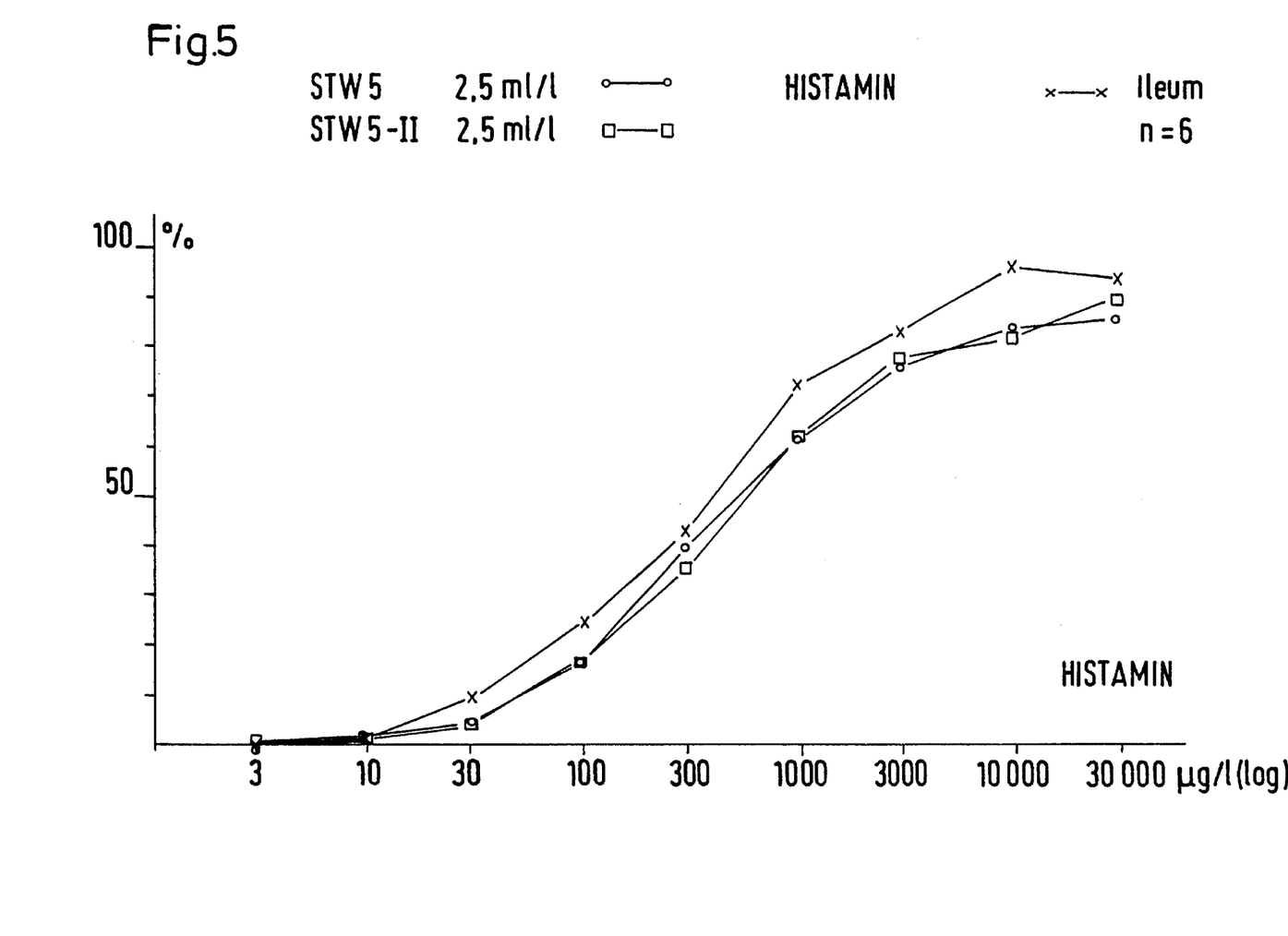
Figure 6:
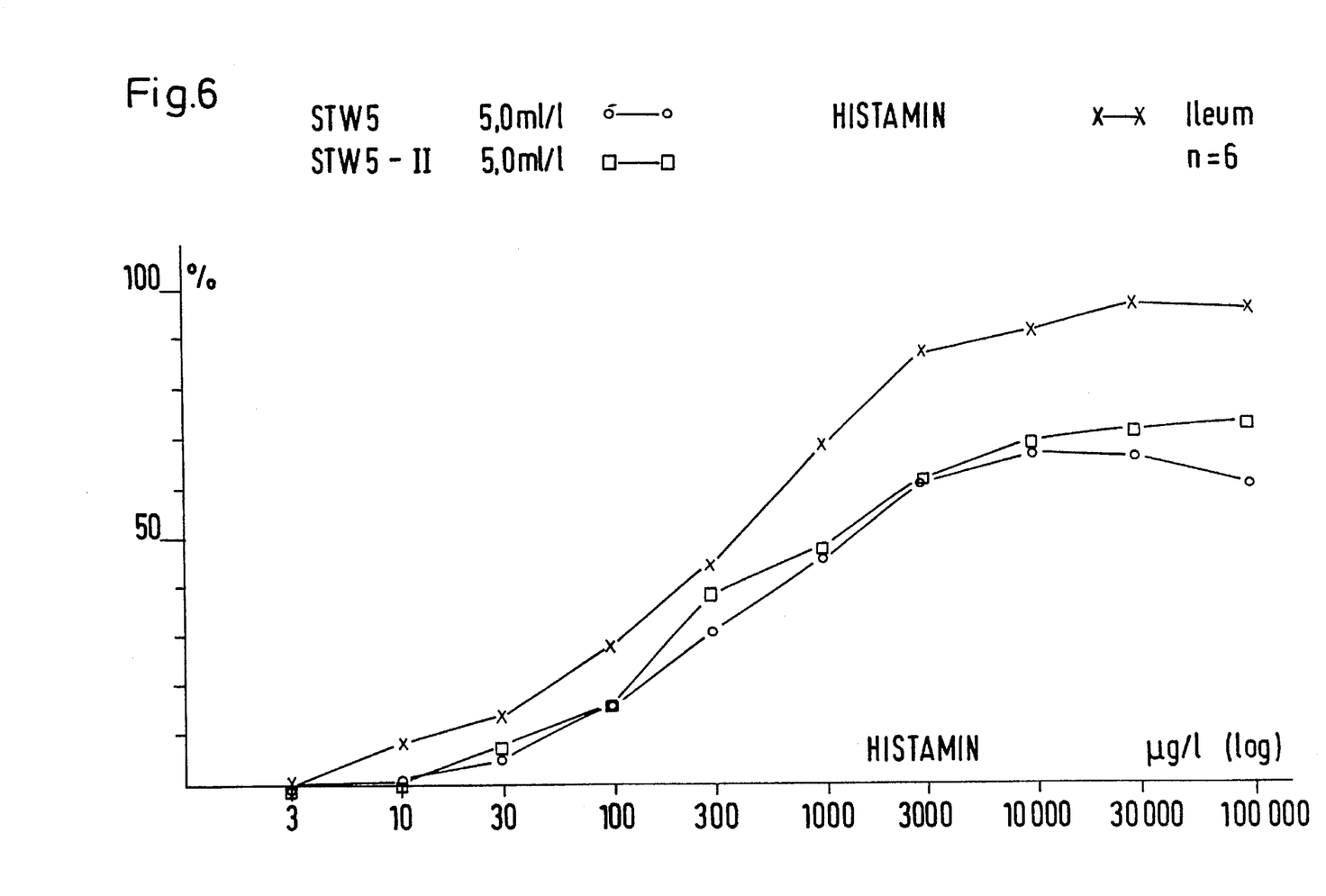
Figure 7:
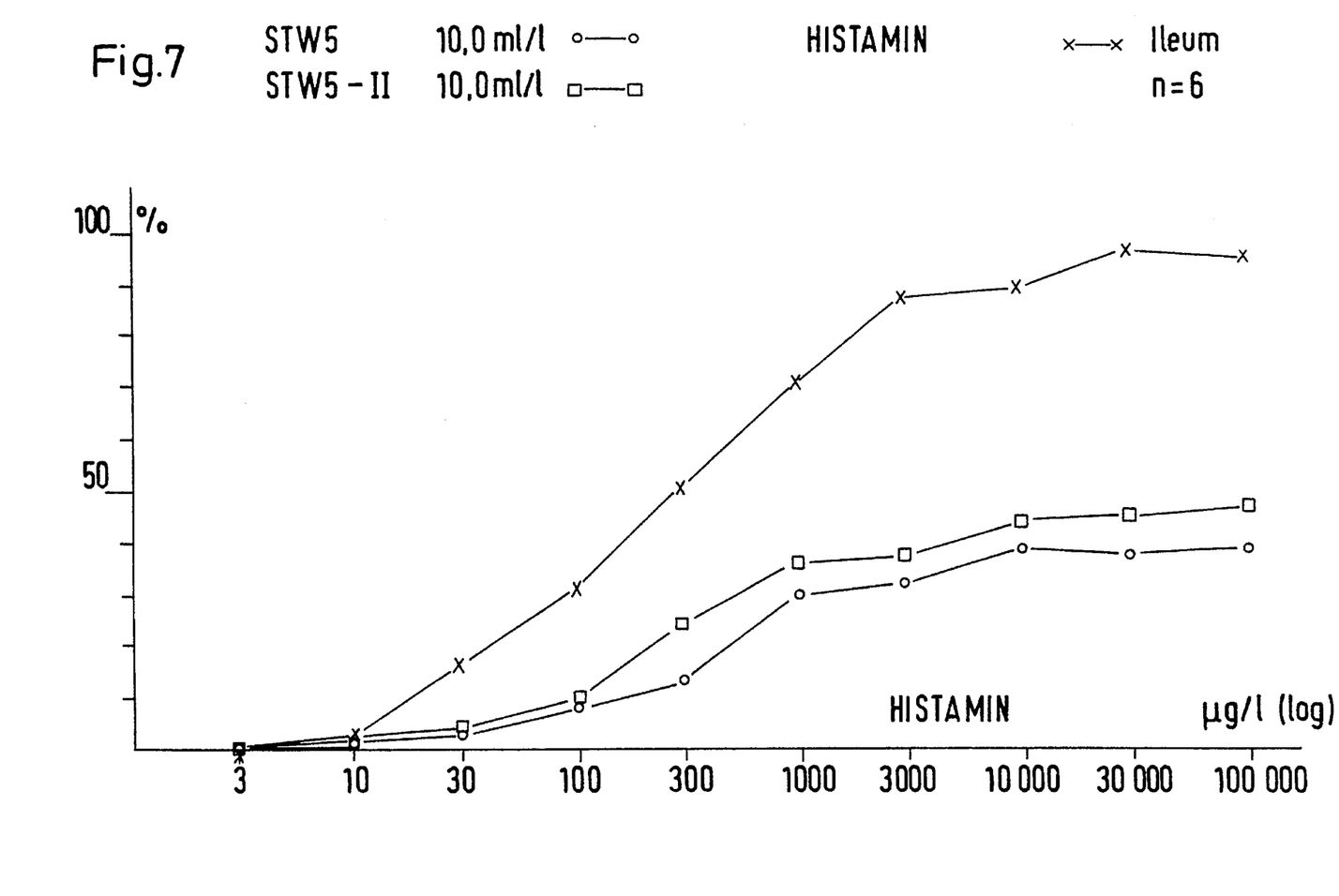

The medicament according to the invention STW 5-II has a distinct basal tone-increasing effect in the hypotonic piece of intestine and has a stronger action than the known product (STW 5).

Spasmolytic Action

The spasmolytic action of the medicament (STW 5-II) was investigated on histamine-induced contraction (spasms) of the guinea-pig ileum and compared with that of the known former product in the same ileum pieces.

The dose-response curves presented in FIGS. 4 to 7 show that the medicament STW 5-II is effective in a dose-dependent and statistically significant spasmolytic (antispasmodic) manner against histamine-induced contraction of the guinea-pig ileum. This activity is comparable at all dosages with that of the former product, but with a distinctly decreased number of constituents.

Motility of the Gastrointestinal Tract (STW 5-II)

The action of the medicament according to the invention comprising *Iberis amara* and one or more constituents selected from the group consisting of *Menthae piperitae*, Matricariae, *Carvi fructus, Melissae folium* and *Liquiritiae radix* as the sole carriers of activity on the motility of the gastrointestinal tract was investigated in minipigs from Alaska-Hoke by the methods described previously. In addition to the determination of the motility of the stomach and of the intestine, pH, acidity, tissue histamine, mast cells and prostaglandins ($PGE_2$) were measured before and after administration of the preparations.

From the results in Table 4 it can be inferred that the medicament combination according to the invention comprising *Iberis amara* and one or more constituents selected from the group consisting of *Menthae piperitae*, Matricariae, *Carvi fructus, Melissae folium* and *Liquiritiae radix* as the sole carriers of activity increases the motility of the hypotonic stomach and of the intestine in a statistically significant manner. The histamine release and mast cell proliferation provoked by acetylsalicylic acid are also inhibited in a statistically significant manner as a sign of the anti-inflammatory and cytoprotective action.

A comparison of this effect with that of the known product (STW 5) (Table 5) makes it clear that the activity of the medicament according to the invention comprising *Iberis amara* as the sole carrier of activity and medicament according to the invention comprising *Iberis amara* and one or more constituents selected from the group consisting of *Menthae piperitae*, Matricariae, *Carvi fructus, Melissae folium* and *Liquiritiae radix* as the sole carriers of activity are to be classified as significantly stronger.

Effect on the 5-Lipoxygenase Products ($LTB_4$)

Both the prostaglandins (in particular $PGE_2$), cyclooxygenase products from the arachidonic acid cascade and the leukotrienes ($LTB_4$), the lipoxygenase metabolites, belong to the mediators of humoral inflammation whose inhibition would be highly desirable in ulcerating gastrointestinal, dyspeptic disorders.

The effects on the 5-lipoxygenase products ($LTB_4$) by the medicament according to the invention comprising *Iberis amara* and one or more constituents selected from the group consisting of *Menthae piperitae*, Matricariae, *Carvi fructus, Melissae folium* and *Liquiritiae radix* as the sole carriers of activity was measured by means of HPLC on activated polymorphonuclear, neutrophilic granulocytes of the rat in vitro after stimulation with calcium ionophore A23187.

If the amount produced in the control experiment is made equal to 100%, the following values are obtained in % X±SD for the test substances:

|         |         | Inhibition |
|---------|---------|------------|
| STW 5   | 89 ± 19 | 11%        |
| STW 6   | 96 ± 7  | 4%         |
| STW 5-II| 75 ± 8  | 25%        |

The action of the medicament according to the invention comprising *Iberis amara* and one or more constituents selected from the group consisting of *Menthae piperitae*, Matricariae, *Carvi fructus, Melissae folium* and *Liquiritiae radix* as the sole carriers of activity in inhibition of the 5-lipoxygenase products is also stronger than that of the former product.

Anti-inflammatory Action

The carrageenan oedema model of the rat is an internationally recognised pharmacological method for uncovering clinically relevant anti-inflammatory agents.

The test substances were administered ½ h before induction of oedema; the control animals received the solvent (30% ethanol). The paw volume was measured with a plethysmometer before (0 value) oedema induction and 1, 2, 3, 4 and 6 hours after.

The anti-inflammatory action of the test substances was calculated according to the formula $$\% \text{ inhibition} = 100 - \left( \frac{V}{K} \cdot 100 \right)$$

V=average value of the differences from the 0 value: drug group

K=average value of the differences from the 0 value; control group

The following results were obtained (% inhibition):

|                                    | 1    | 2    | 3     | 4     | 6 h   |
|                                    |      |      | after oedema induction | | |
|------------------------------------|------|------|-------|-------|-------|
| STW 5 5 ml/kg of body wt.:         | 24.0 | 20.6 | 25.0* | 37.5  | 38.7  |
| STW 5-II 5 ml/kg of body wt.:      | 4.0  | 14.7 | 27.5* | 35.0* | 38.7* |
| Indomethacin 4 mg/kg of body wt.:  | 24.0 | 23.5 | 35.0* | 47.5* | 61.3* |

*P ≤ 0.05

The results show that medicament according to the present invention has a statistically significant anti-inflammatory action in the critical inflammation phase (3 to 6 hours after induction) and that this activity is of the order of magnitude of that of the former product and can be compared with that of the chemical substance indomethacin.

In addition to the dual action of tone/motility regulation, the medicament according to the invention has a distinct anti-inflammatory potential owing to inhibition of the cyclo- and lipoxygenase products which occur in dyspeptic or functional and motility-related gastrointestinal disorders due to damage to the mucous membranes (gastritis, colitis, ulcers and the like).

As a tone modulator, plant-based medicament according to to the present invention combines the advantages of a spasmolytic and a spasmodic (prokinetic) with the properties of an anti-inflammatory agent.

TABLE 1

| Iberis Amara (STW 6) n = 6 | | |
|---|---|---|
| | before | after |
| pH | 1.8 ± 0.1 | 1.6 ± 0.2 |
| Acidity | 24 ± 4 | 26 ± 3 |
| Tissue histamine | 33 ± 4 | 36 ± 4 |
| Provocation | 34 ± 4 | 24 ± 2** |
| Mast cells | — | 62 ± 6 |
| Provocation | 59 ± 3 | 45 ± 4** |
| PGE$_2$ | 14 ± 3 | 13 ± 4 |
| Provocation | 10 ± 2 | 10 ± 3 |
| Gastric motility | 5 ± 3 | 8 ± 2* |
| Intestinal motility | 10 ± 4 | 14 ± 3* |

\* = $p < 0.05$
\*\* = $p < 0.005$

TABLE 2

Increase in basal tone
Test substance STW 5-11

| Concentration (ml/l) | Expt. 1 | Expt. 2 | Expt. 3 | Expt. 4 | Expt. 5 | Expt. 6 |
|---|---|---|---|---|---|---|
| 1.25 | 0.0 | 0.0 | 0.0 | 0.5 | 0.0 | 0.0 |
| 2.5 | 2.0 | 0.1 | 0.4 | 0.6 | 0.1 | 0.0 |
| 5.0 | 1.0 | 0.2 | 1.1 | 1.2 | 0.0 | 0.7 |
| 10.0 | 2.0 | 0.3 | 2.1 | 3.4 | 0.2 | 1.5 |
| 20.0 | 3.0 | 0.4 | 5.4 | 6.0 | 0.4 | 2.3 |
| 40.0 | 3.0 | 0.6 | 5.1 | 6.0 | 0.3 | 1.9 |
| Acetylch. 40 µg/l | 10.1 | 14.6 | 11.7 | 14.0 | 12.7 | 8.6 |

| Average values Concentration (ml/l) | Average value | SEM | Number |
|---|---|---|---|
| 1.25 | 0.08 | 0.08 | 6 |
| 2.5 | 0.53 | 0.28 | 6 |
| 5.0 | 0.70 | 0.19 | 6 |
| 10.0 | 1.58 | 0.45 | 6 |
| 20.0 | 2.92 | 0.89 | 6 |
| 40.0 | 2.82 | 0.87 | 6 |
| Acetylch. 40 µg/l | 11.95 | 0.86 | 6 |

TABLE 3

Increase in basal tone
Test substance STW 5

| Concentration (ml/l) | Expt. 1 | Expt. 2 | Expt. 3 | Expt. 4 | Expt. 5 | Expt. 6 |
|---|---|---|---|---|---|---|
| 1.25 | 0.3 | 0.0 | 1.8 | 0.1 | 0.3 | 0.3 |
| 2.5 | 0.3 | 0.0 | 2.6 | 0.0 | 0.8 | 0.7 |
| 5.0 | 0.3 | 0.2 | 2.4 | 0.1 | 0.8 | 0.5 |
| 10.0 | 0.2 | 0.1 | 3.2 | 0.1 | 1.7 | 1.1 |
| 20.0 | 0.2 | 0.0 | 2.6 | 0.3 | 0.9 | 1.2 |
| 40.0 | 0.1 | 0.0 | 0.8 | 0.1 | 0.1 | 0.0 |
| Acetylch. 40 µg/l | 11.8 | 6.3 | 12.1 | 9.9 | 12.2 | 5.9 |

| Average values Concentration (ml/l) | Average value | SEM | Number |
|---|---|---|---|
| 1.25 | 0.47 | 0.25 | 6 |
| 2.5 | 0.73 | 0.36 | 6 |
| 5.0 | 0.72 | 0.32 | 6 |
| 10.0 | 1.07 | 0.46 | 6 |
| 20.0 | 0.87 | 0.36 | 6 |
| 40.0 | 0.18 | 0.11 | 6 |
| Acetylch. 40 µg/l | 9.70 | 1.09 | 6 |

TABLE 4

| Fol. Melissae Fruct. Carvi Flor. Chamomillae Iberis amara Fol. Menthae pip. | Combination STW 5-II n = 6 | |
|---|---|---|
| | before | after |
| pH | 1.4 ± 0.2 | 2.2 ± 0.4 |
| Acidity | 22 ± 4 | 29 ± 5 |
| Tissue histamine | 32 ± 5 | 37 ± 6 |
| Provocation | 36 ± 6 | 30 ± 7* |
| Mast cells | 64 ± 6 | 61 ± 3 |
| Provocation | 68 ± 7 | 54 ± 6* |
| PGE$_2$ | 10 ± 4 | 17 ± 3** |
| Provocation | 13 ± 4 | 12 ± 4 |
| Gastric motility | 5 ± 2 | 11 ± 3** |
| Intestinal motility | 10 ± 2 | 11 ± 3** |

TABLE 5

| Known product (STW 5) | | |
|---|---|---|
| | before | after |
| pH | 1.4 ± 0.3 | 1.9 ± 0.4 |
| Acidity | 26 ± 5 | 29 ± 4 |
| Tissue histamine | 37 ± 5 | 32 ± 4 |
| Provocation | 34 ± 5 | 24 ± 6** |
| Mast cells | 61 ± 4 | 58 ± 5 |
| Provocation | 58 ± 5 | 44 ± 5** |
| PGE$_2$ | 12 ± 3 | 15 ± 4 |
| Provocation | 14 ± 2 | 12 ± 3 |
| Gastric motility | 6 ± 4 | 9 ± 4 |
| Intestinal motility | 9 ± 4 | 14 ± 5 |

Although medicament and methods in accordance with the present invention have been described herein in connection with preferred embodiments, it will be appreciated by those skilled in the art that modifications not specifically described may be made without departing from the spirit and scope of the invention defined in the claims.

I claim:

1. A plant-based medicament having tonicising action on smooth muscular organs which are atonic or have decreased tone, comprising *Iberis amara* together with at least one other constituent selected from the group consisting of extracts of

*Menthae piperitae,*

Matricariae,

*Carvi fructus,*

*Melissae folium,* and

*Liquiritiae radix,* as the sole carriers of the activity in combination with a pharmaceutically acceptable carrier, wherein said *Iberis amara* is selected from the group consisting of *Iberis amara* seeds, *Iberis amara* flowers, *Iberis amara* leaves, *Iberis amara* stalks, *Iberis amara* roots, an extract of *Iberis amara* or a combination thereof.

2. A plant-based medicament according to claim 1, wherein said *Iberis amara* is *Iberis amara* totalis.

3. A plant-based medicament according to claim 1, wherein said *Iberis amara* is an extract of *Iberis amara*.

4. The medicament according to claim 3, wherein said extract is prepared using a ratio of plant material to extracting agent of about 1.5 to 5 grams:10 grams.

5. The medicament according to claim 3, wherein said plant extract is obtained using an ethanol and $H_2O$ extracting agent, and wherein said ethanol is present in said extracting agent a final concentration of 30–40% by volume.

6. The medicament according to claim 3, wherein dried plant material is used in said plant extract, and wherein the ratio of dried plant material to extract is about 3.5 grams:10 grams.

7. The plant-based medicament according to claim 3, wherein said medicament comprises fresh plant extract.

8. The medicament according to claim 7, wherein in said fresh plant extract, the ratio of macerated or percolated plant to the extract is about 3 to 7 grams:10 grams.

9. The medicament according to claim 7, wherein in said fresh plant extract, the ratio of macerated or percolated plant to the extract is about 6 grams:10 grams.

10. The medicament according to claim 1, wherein said medicament comprises

15–40% by volume of *Iberis amara,*

10–30% by volume of *Menthae piperitae,*

20–40% by volume of Matricariae,

10–30% by volume of *Carvi fructus,*

10–30% by volume of *Melissae folium* and

10–30% by volume of *Liquiritiae radix.*

11. The medicament according to claim 1, wherein said medicament comprises

15% by volume of *Iberis amara* totalis,

10% by volume of *Menthae piperitae* folium,

30% by volume of *Matricariae flos,*

20% by volume of *Carvi fructus,*

15% by volume of *Melissae folium* and

10% by volume of *Liquiritiae radix.*

12. A method of modulating or regulating the tone or motility of an organ of a patient in need of such action, the method comprising administering to said patient a tonicising effective amount of a plant-based medicament comprising *Iberis amara* as the sole carrier of the activity, wherein said *Iberis amara* is selected from the group consisting of *Iberis amara* seeds, *Iberis amara* flowers, *Iberis amara* leaves, *Iberis amara* stalks, *Iberis amara* roots, an extract of *Iberis amara* or a combination thereof.

13. A method according to claim 12, wherein said *Iberis amara* is *Iberis amara* totalis.

14. A method of modulating or regulating the tone or motility of an organ of a patient in need of such action, the method comprising administering to said patient a tonicising effective amount of a plant-based medicament comprising *Iberis amara* together with at least one other constituent selected from the group consisting of extracts of

*Menthae piperitae,*

Matricariae,

*Carvi fructus,*

*Melissae folium,* and

*Liquiritiae radix,* as the sole carriers of the activity, wherein said *Iberis amara* is selected from the group consisting of *Iberis amara* seeds, *Iberis amara* flowers, *Iberis amara* leaves, *Iberis amara* stalks, *Iberis amara* roots, an extract of *Iberis amara* or a combination thereof.

15. The method according to claim 14, wherein said medicament comprises

15–40% by volume of *Iberis amara,*

10–30% by volume of *Menthae piperitae,*

20–40% by volume of Matricarieae,

10–30% by volume of *Carvi fructus,*

10–30% by volume of *Melissae folium* and

10–30% by volume of *Liquiritiae radix.*

16. The method according to claim 15, wherein said medicament comprises

15% by volume of *Iberis amara* totalis,

10% by volume of *Menthae piperitae* folium,

30% by volume of *Matricariae flos,*

20% by volume of *Carvi fructus,*

15% by volume of *Melissae folium* and

10% by volume of *Liquiritiae radix.*

17. The method according to claim 14, wherein said *Iberis amara* is *Iberis amara* totalis.

* * * * *